US006415034B1

(12) United States Patent
Hietanen

(10) Patent No.: US 6,415,034 B1
(45) Date of Patent: *Jul. 2, 2002

(54) EARPHONE UNIT AND A TERMINAL DEVICE

(75) Inventor: Jarmo Hietanen, Tampere (FI)

(73) Assignee: Nokia Mobile Phones Ltd., Espoo (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/906,371

(22) Filed: Aug. 4, 1997

(30) Foreign Application Priority Data

Aug. 13, 1996 (FI) ................................................ 963173

(51) Int. Cl.[7] ......................... A61F 11/06; G10K 11/16; H04R 25/00

(52) U.S. Cl. ....................... 381/71.6; 381/326; 381/151

(58) Field of Search ................................ 381/370, 375, 381/380, 71.6, 23.1, 60, 317, 318, 320, 326, 71.1, 72, 74, 92, 94.1, 151, 66, 372; 379/430; 181/127, 128

(56) References Cited

U.S. PATENT DOCUMENTS 3,995,113 A 11/1976 Tani ........................... 179/1 P
4,975,967 A * 12/1990 Rasmussen ................. 381/380
5,099,519 A 3/1992 Guan ......................... 381/183
5,285,165 A 2/1994 Renfors et al. ............. 328/167
5,298,692 A * 3/1994 Ikeda et al. ................. 381/380
5,313,661 A 5/1994 Malmi et al. ............ 455/232.1
5,343,523 A 8/1994 Bartlett et al. .............. 379/430
5,406,635 A 4/1995 Jarvinen ...................... 381/94
5,426,719 A 6/1995 Franks et al. .............. 395/2.37
5,692,059 A * 11/1997 Kruger ....................... 381/151
5,732,143 A * 3/1998 Andrea et al. ............. 381/71.6
5,748,725 A * 5/1998 Kubo ........................ 381/71.1
5,790,684 A * 8/1998 Niino et al. ................ 381/326
5,909,498 A * 6/1999 Smith ......................... 381/380
5,933,506 A * 8/1999 Aoki et al. ................. 381/151

FOREIGN PATENT DOCUMENTS

| | | |
|---|---|---|
| EP | 0637187 A1 | 2/1995 |
| GB | 2226931 | 7/1990 |
| GB | 2281004 | 2/1995 |
| WO | WO 94/06255 | 3/1994 |

OTHER PUBLICATIONS

Journal of Sound And Vibration, 1994, vol. 174, pp. 617–639, "Simultaneous Piezoelectric Sensing/Actuation: Analysis And Application to Controlled Structures", Anderson et al.

Advanced Engineering Mathematics, sixth edition, pp. 271 & 272, "Convolution. Integral Equations", Erwin Kreyszig.

* cited by examiner

*Primary Examiner*—Xu Mei
(74) *Attorney, Agent, or Firm*—Perman & Green, LLP

(57) ABSTRACT

The scope of the present invention is an earphone unit (11) to be mounted either on external ear (18) or in auditory tube (10), in which unit both a speech registering microphone (13) and a speech reproducing ear capsule (12) have been placed. The earphone unit (11) is suitable for use in connection with various terminal devices, in particular with mobile stations. When a user's speech is registered, the ear capsule signal (12') containing disturbances is canceled utilizing methods based upon determining the transfer function between the ear capsule (12) and the microphone (13). A separate error microphone (14) is used for eliminating external sources of disturbances (17), such as noise. In order to improve the quality of speech and prevent problems caused by double-talk, signals (15', 12', 17') are processed digitally utilizing e.g. band limitation and prediction of missing bands.

13 Claims, 7 Drawing Sheets

EARPHONE UNIT AND A TERMINAL DEVICE

FIELD OF THE INVENTION

The present invention relates to an earphone unit mounted in the auditory tube (also called auditory canal) or on the ear, which unit comprises voice reproduction means for converting an electric signal into acoustic sound signal and for forwarding the sound signal into the user's ear, and speech detection means for detecting the speech of the user of the earphone unit from the user's said same auditory tube. The earphone unit is suitable for use in connection with a terminal device, especially in connection with a mobile station. In addition to above the invention is related to a terminal device incorporating or having a separate earphone unit and to a method of reproduction and detection of sound.

BACKGROUND OF THE INVENTION

Traditional headsets equipped with a microphone have an earpiece for either both ears or only for one ear, from which earpiece in general a separate microphone bar extending to mouth or the side of mouth is protruding. The earpiece is either of a type to be mounted on the ear or in the auditory tube. The microphone used is air connected, either a pressure or a pressure gradient microphone. The required amplifiers and other electronics are typically placed in a separate device. If a wireless system is concerned, it is possible to place some of the required electronics in connection with the earpiece device, and the rest in a separate transceiver unit. It is also possible to integrate the transceiver unit in the earpiece device.

Patent publication U.S. Pat. No. 5,343,523 describes an earphone solution designed for pilots and telephone operators, in which earpieces are mounted on the ears and a separate microphone suspended from a bar is mounted in front of the mouth. In addition to above, a separate error microphone has been arranged in connection with the earpieces, by utilizing which microphone some of the environmental noise detected by the user can be cancelled and the intelligibility of speech can be improved in this way.

Alternative solutions have been developed for occasions in which a separate microphone suspended from a bar cannot be used. Detection of speech through soft tissue is prior known e.g. from throat microphones used in tank headgear. On the other hand, detection of speech through the auditory tube has been presented in patent publication U.S. Pat. No. 5,099,519. In said patent publication it has been said that the advantages of speech detection through the auditory tube are the small size of the earpiece and the suitability of the device to noisy environment. A microphone closing the auditory tube acts also as an elementary hearing protector.

Patent publication U.S. Pat. No. 5,426,719 presents a device which also acts as a combined hearing protector and as a means of communication. In said patent publication, as well as also in the above mentioned patent publication U.S. Pat. No. 5,099,519, the microphone is placed in one earpiece and the ear capsule respectively in the other earpiece. This means that a device according to any of the two patent publications requires using both ears, which makes the device bulky and limits the field of use of the device.

Patent publication WO 94/06255 presents an ear microphone unit for placement in one ear only. The unit is mounted in a holder for placement in the outer ear. For use in full duplex ear communication the holder further has a sound generator. Between the sound generator and the microphone is mounted a vibration absorbing unit. Also the sound generator is embedded in a thin layer of attenuation foam.

Another device for two-way acoustic communication through one ear is described in patent publication U.S. Pat. No. 3,995,113. This device is based on an electro-acoustic mutual transducing device adapted to be inserted into the auditory canal and which can function both as a speaker and microphone. It forms an ear-plug type transmitting-receiving device. The device additionally includes means for reducing the mechanical impedance of the vibrating system and a means for eliminating the noise resulting from said impedance reducing means.

SUMMARY OF THE INVENTION

Now an improved earphone unit has been invented, which unit facilitates placing of a microphone and an ear capsule in same auditory tube or on the same ear and which has means for eliminating sounds produced into the auditory tube by the ear capsule from sounds detected by the microphone. This improves the detection of the user's speech, which is registered via the auditory tube, especially when the user speaks simultaneously as sound is reproduced by the ear capsule. In telephones, such as mobile phones this is needed especially in double talk situations, i.e. when both the near end and far end speaker speak simultaneously. It is possible to install in the earphone unit also a separate error microphone for elimination of external disturbances. It is possible to use for microphones and ear capsules any means of conversion prior known to a person skilled in the art that convert acoustic energy into electric form (microphone), and electric energy into acoustic form (ear capsule, loudspeaker). The invention presents a new solution for determining the acoustic coupling of a microphone and a loudspeaker and for optimizing voice quality using digital signal processing.

The earphone unit according to the invention is suitable for use in occasions in which environmental noise prevents from using a conventional microphone placed in front of mouth. Respectively, the small size of the earphone unit according to the invention enables using the device in occasions in which small size is an advantage e.g. due to inconspicuousnes. In this way the earphone unit according to the invention is particularly suitable for use e.g. in connection with a mobile station or a radio telephone while moving in public places. The use of the earphone unit is not limited to wireless mobile stations, but it is equally possible to use the earphone unit in connection with even other terminal devices. One preferable field of use is to connect the earphone unit to a traditional telephone or other wire-connected telecommunication terminal device. It is equally possible to use the earphone unit according to the invention in connection with various interactive computer programs, radio tape recorders and dictating machines. It is also possible to integrate the earphone unit as a part of a terminal device as presented in the embodiments below.

When an attempt is made to detect from the auditory tube simultaneously speech of very low sound pressure level and sound is fed with relatively high sound pressure level into the same ear using the ear capsule, problems arise when analogue summing units and amplifiers equipped with fixed adjustments are used. In this system the auditory tube is an important acoustic component, because it has an effect upon both the user's speech and on the voice produced by the ear capsule. Because the auditory tube of each person is unique, the transfer function between the microphone and the ear capsule is individual. In addition to this the transfer function is different each time the earphone unit is set into place, because the ear capsule may be set e.g. at a different depth. If the setting of the earphone unit is not completely successful, the acoustic leakage of the ear capsule may be beyond control, which can disturb the operation of the device. An acoustic leakage means e.g. a situation in which environmental noise leaks past an ear capsule placed in the auditory tube into the auditory tube. If an earphone unit according to the invention consisting of a microphone and an ear capsule is placed in a separate device outside the auditory tube, it is particularly important to have the acoustic leakage under control.

In order to be able to separate the sound components produced by various sources of noise, which components are disturbing and unnecessary from the point of view of the intelligibility and clearness of the user's speech and in order to be able to remove them from the signal detected by the microphone in such a way that essentially just the user's voice remains, the transfer functions between the various components of the system must be known. Because the transfer function between the microphone capsule and the ear capsule is not constant, the transfer function must be monitored. Monitoring of the transfer function can be carried out e.g. through measurements based on noise. In order to improve voice quality and the intelligibility of speech, it is possible to divide the detection and reproduction of speech in various frequency bands which are processed digitally.

It is characteristic of the ear-connectable earphone unit and the terminal device arrangement according to the invention that it comprises means for eliminating sounds produced into the auditory tube by said sound reproduction means from sounds detected by said speech detection means.

It is characteristic of the terminal device according to the invention that said sound reproduction means and said speech detection means have been arranged in the terminal device close to each other in a manner for connecting both simultaneously to one and the same ear of a user, and the terminal device further comprising means for eliminating sounds produced into the auditory tube by said sound reproduction means from sounds detected by said speech detection means.

It is characteristic of the method according to the invention that disturbance caused in the ear by the first sound signal is subtracted from said second sound signal.

BRIEF DESCRIPTION OF THE DRAWINGS

The invention is described in detail in the following with reference to enclosed figures, of which

DETAILED DESCRIPTION

Figure 1:
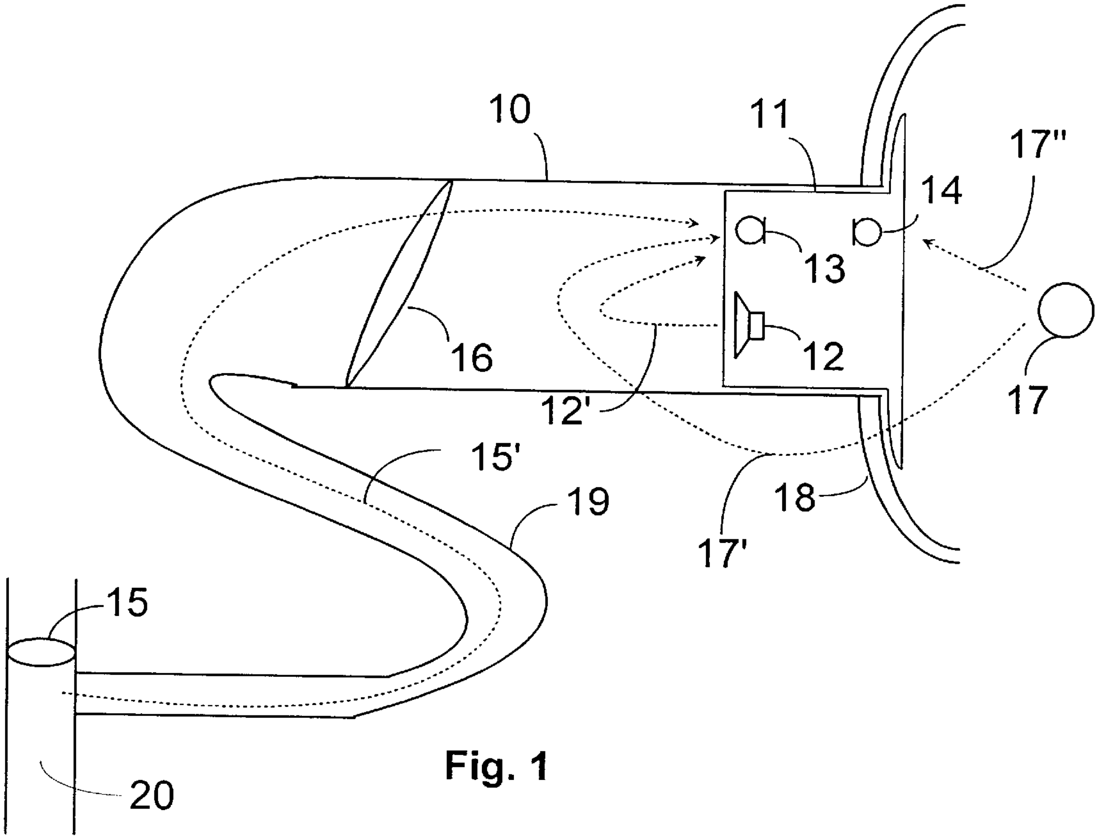
FIG. 1 presents both the components of the earphone unit according to the invention and its location in the auditory tube.

In the following the invention is explained based upon an embodiment. FIG. 1 presents earphone unit 11 according to the invention, which makes it possible to place microphone capsule 13 and ear capsule 12 in same auditory tube 10. Error microphone 14 is located on the outer surface of earphone unit 11. Earphone unit 11 has been given such a form that intrusion of external noise 17' into auditory tube 10 has been prevented as efficiently as possible. External noise 17' consists of e.g. noise produced by working machinery and speech of persons nearby. The source of noise is in FIG. 1 represented by block 17 and the sound advancing from source of noise 17 directly to error microphone 14 is presented with reference 17". The advantage of earphone unit 11 is its small size and its suitability for noisy environment.

Figure 2A:
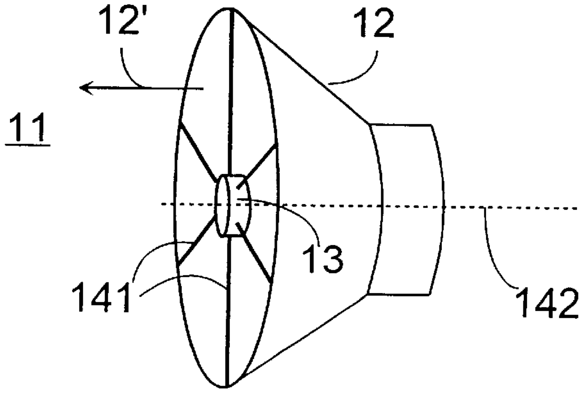
FIGS. 2A and 2B present various ways of placing, in relation to each other, the microphones and the ear capsule used in the earphone unit according to the invention.
Figure 2B:
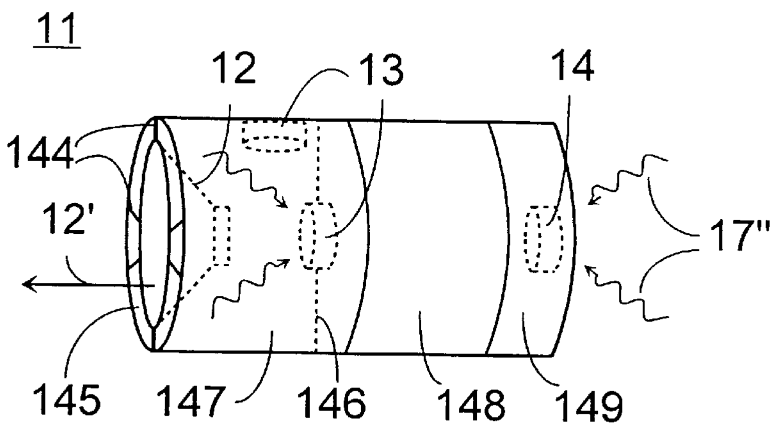
Figure 2C:
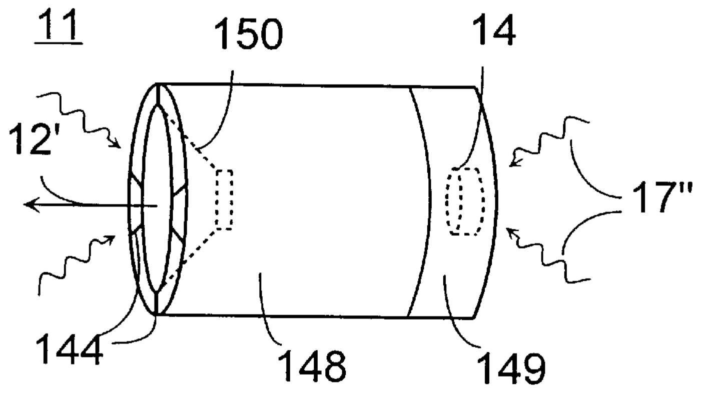
FIG. 2C presents the realization of the earphone unit according to the invention utilizing a dynamic ear capsule.

Microphone capsule 13 and ear capsule 12 can be physically located in relation to each other in a number of ways. FIGS. 2A and 2B present alternative placing of microphone capsule 13, error microphone 14 and ear capsule 12, and FIG. 2C presents utilizing of dynamic ear capsule 150 as both microphone capsule 13 and ear capsule 12. In FIG. 2A microphone capsule 13 has as an example been placed in front of ear capsule 12 close to acoustic axis 142. It is possible to integrate microphone capsule 13 in the body of ear capsule 12, or it can be mounted using supports 141. Arrow 12' presents sound emitted by ear capsule 12.

Figure 4:
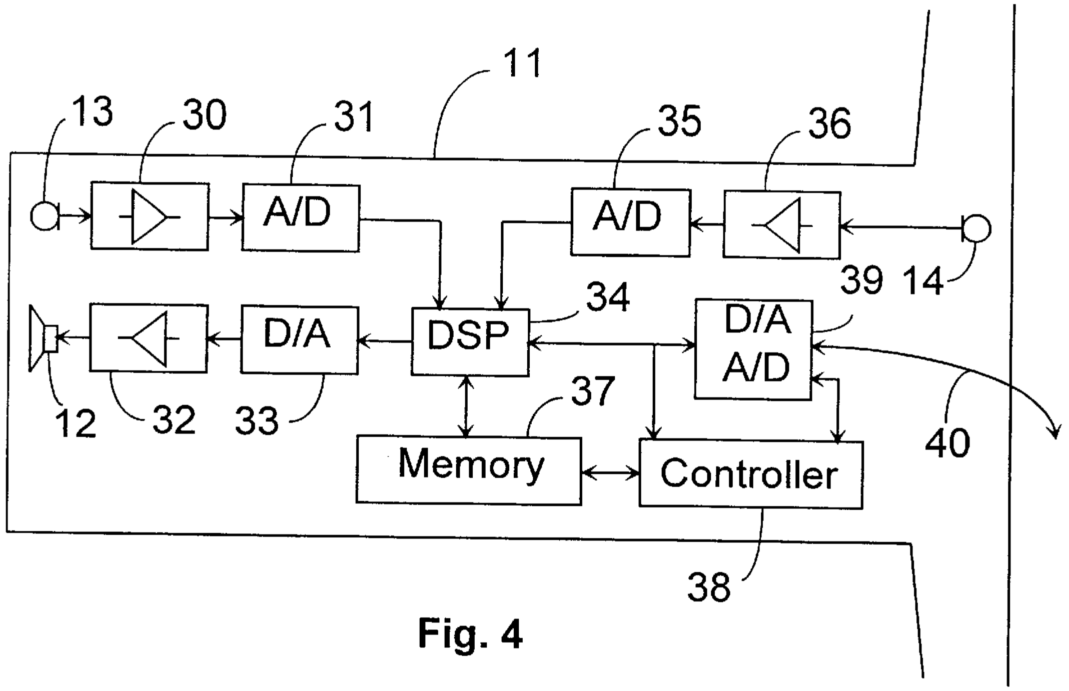
FIG. 4 presents as a block diagram the components and connections of an earphone unit according to the invention.

FIG. 2B presents a solution in which ear capsule 12 has been installed in the other, auditory tube 10 side, end of earphone unit 11. Ear capsule 12 is integrated in the body of earphone unit 11 e.g. using supports 144. Slots or apertures 145 have been arranged between the housing of earphone unit 11 and supports 144 to the otherwise closed microphone chamber in which microphone capsule 13 has been placed. Microphone capsule 13 is integrated in the body of earphone unit 11 or fixed solidly on e.g. supports 146. Space 148 has been arranged behind microphone chamber 147 for electric components required by earphone unit 11, such as processor 34, amplifiers and A/D and D/A-converters (FIG. 4). Error microphone 14 which has an acoustic connection to noise 17" arriving from the source of noise 17 has been placed in space 149 in the end of earphone unit 11 opposite to ear capsule 12.

FIG. 2C presents an embodiment of earphone unit 11, in which separate ear capsule 12 and microphone capsule 13 have been replaced with dynamic ear capsule 150 which is capable of acting simultaneously as a sound reproducing and receiving component. It is possible to use instead of dynamic ear capsules 150 e.g. a piezoelectric converters, which have been described in more detail in publication Anderson, E. H. and Hagood, N. W. 1994 Simultaneous piezoelectric sensing/actuation: analysis and applications to controlled structures, Journal of Sound and Vibration, vol 174, 617–639. The solution of integrating ear capsule 12 and microphone capsule 13 preferably reduces the need for space of earphone unit 11. Such a construction is also simpler in its mechanical realization. It is also possible to use in the earphone unit 11 according to the invention other ways of placing and realizing microphones 13 and 14 and ear capsule 12, different in their realization.

The human speech is generated in the larynx 20 (FIG. 1) in the upper end of the windpipe, in which the vocal cords 15 are situated. From the vocal cords 15 the speech is transferred through the Eustachian tube connecting the throat and the middle ear to the eardrum 16. Also connected to the eardrum 16 are the auditory ossicles (not shown in the figure) in the middle ear, over which the sound is forwarded into the inner ear (not shown in the figure) where the sensing of sound takes place. The yibrations of the eardrum 16 relays the speech through the auditory tube 10 to the microphone capsule 13 in the auditory tube 10 end of earphone unit 11. When speech is transferred to the user of earphone unit 11 over ear capsule 12, this speech is sensed by the eardrum 16.

Figure 3:
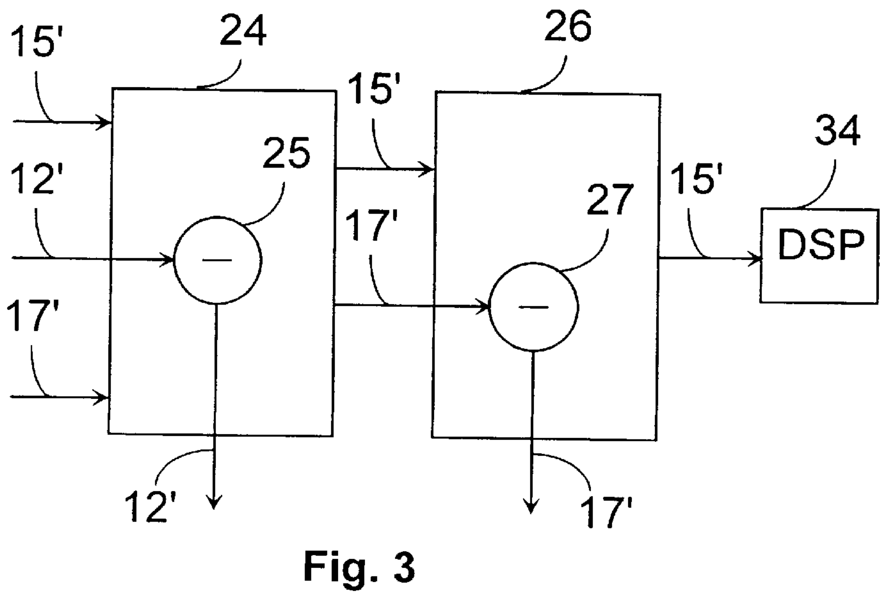
FIG. 3 presents as a block diagram separating the sounds produced by the ear capsule and sounds produced by external noise from a detected microphone signal.

In FIG. 3, block 24 illustrates sound signals received by microphone capsule 13. They consist of three components: speech signal 15' originated in the vocal cords, ear capsule signal 12' reproduced by ear capsule 12 in the auditory tube 10 and noise signal 17" caused by external sources of noise 17. In order to be able to detect the desired speech signal 15' in the auditory tube 10 in the best possible way, signals 12' and 17', which are disturbing from the point of view of speech signal 15', are strived to be eliminated e.g. in two different stages. In the first stage ear capsule signal 12' generated by ear capsule 12 in the auditory tube 10 is removed in block 24. Because the original electric initiator of ear capsule signal 12' is known, it can be subtracted from the signal received by microphone capsule 13 using subtractor 25 provided that the transfer function between ear capsule 12 and microphone capsule 13 is known. Because the transfer function between error microphone 14 and microphone capsule 13 is essentially constant, noise signal 17' can be subtracted in second stage 25 using subtractor 27 using a method which is explained later.

Figure 5:
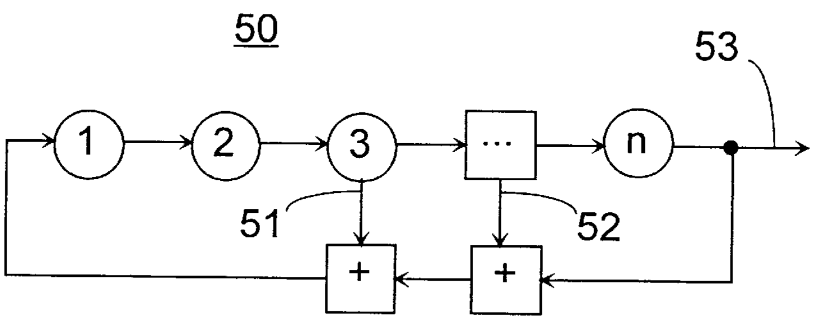
FIG. 5 presents the digital shift register equipped with feed-back used for forming an MLS-signal.

The transfer function between ear capsule 12 and microphone capsule 13 is determined e.g. using so-called MLS (Maximum Length Sequence)-signal. In this method a known MLS-signal is fed into the auditory tube 10 with ear capsule 12, the response caused by which signal is measured with microphone capsule 13. This measuring is executed preferably at such discrete moments when no other information is transferred to the user over ear capsule 12. In principle it is possible to use any sound signal as the known measuring sound signal, but it is nice from the user's point of view to use e.g. the MLS-signal resembling using a generator 50 (FIG. 5) which generates binary, seemingly random sequences (pseudo-random sequence generator), which generator is realized digitally in processor 34 (FIG. 4) in earphone unit 11. FIG. 5 presents the realization of generator 50 using a n-stage shift register. Output 53 of the generator is, with suitably selected feed-backs 51 and 52, binary sequences repeated identically at certain intervals. The sequences are fed to D/A-converter 33 (FIG. 4), and from there further to amplifier 32 and ear capsule 12. The repeating frequency of the sequences depends on the number of stages n of the generator and on the choice of feed-back 51 and 52. The longest possible sequence available using n-stage generator 50 has the length of $2^n-1$ bits. For example a 64-stage generator can produce a sequence which is repeated identical only after 600,000 years when 1 MHz clock frequency is used. It is prior known to a person skilled in the art that such long sequences are generally used to simulate real random noise.

Figure 6:
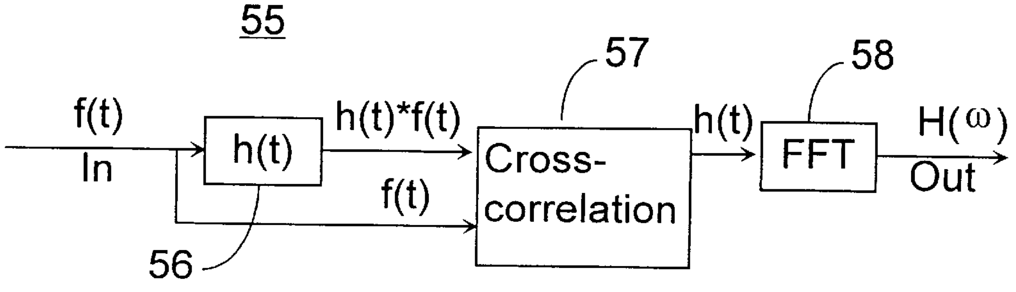
FIG. 6 presents as a block diagram determining the transfer function between a microphone and an ear capsule.

FIG. 6 presents determining the transfer function. Ear capsule 12 is used to feed a known signal f(t) into the auditory tube 10 and the signal is detected using microphone capsule 13. Processor 34 saves the supplied signal f(t) in memory 37. In auditory tube 10 signal f(t) is transformed due to the effect of impulse response h(t) (ref. 56) into form h(t)*f(t). Through microphone capsule 13 and amplifier 30 signal h(t)*f(t) is directed to A/D-converter 31 and saved in memory 37. Signal h(t)*f(t) is a convolution of the supplied signal f(t) and the system impulse response h(t) (ref. 56). Convolution has been described e.g. in Erwin Kreyszig's book Advanced Engineering Mathematics, sixth edition, page 271 (Convolution theorem). The system impulse response h(t) is determined by calculating the cross-correlation, prior known to persons skilled in the art, of the supplied signal f(t) and the received signal h(t)*f(t). Impulse response h(t) in time space can be converted into the form in frequency space e.g. using FFT (Fast Fourier Transform)-transform 58, resulting in system transfer function H(ω). Relatively low signal to noise ratio (SNR) will be sufficient for a successful measuring. The accuracy of the impulse response can, in addition to increasing the SNR, be improved through averaging. In preferable conditions the user will not detect the determining of the impulse response at all.

A microphone signal contains the following sound components:

$$m(t)=x(t)+y(t)+z(t) \tag{1}$$

in which m(t) is the sound signal received by microphone capsule 13 x(t) is desired speech signal 15' y(t) is ear capsule signal 12' detected by microphone capsule 13 z(t) is external noise signal 17' detected by microphone capsule 13.

Because the speech signal x(t) transferred by eardrum 16 is wanted to be solved, the share of ear capsule 12 and of external noise 17 must be subtracted from the microphone signal. In this case equation (1) can be rewritten in form:

$$x(t)=m(t)-y(t)-z(t). \tag{2}$$

Sound component y(t) detected by microphone capsule 13 can be written, utilizing the original known electric signal y'(t) supplied to the ear capsule and the determined impulse response h(t) as follows:

$$y(t)=h(t)*y'(t) \tag{3}$$

By substituting equation (3) into equation (2) it is obtained:

$$x(t)=m(t)-h(t)*y'(t)-z(t) \tag{4}$$

Error microphone 14 is used to compensate for external signal z(t). Error microphone 14 measures external noise z'(t) which is used as a reference signal. When external noise z'(t) reaches microphone capsule 13 it is transformed in a way determined by acoustic transfer function K(ω) between the microphones. Transfer function K(ω) and its equivalent k(t) in time space can be determined most preferably in the manufacturing stage of earphone unit 11, because the coupling between microphones 13 and 14 is constant due to the construction of earphone unit 11. In this case z(t) can be written, using reference signal z'(t) and impulse response k(t) between the microphones as follows:

$$z(t)=k(t)*z'(t) \quad (5)$$

By substituting equation (5) into equation (4), by processing the microphone signal m(t) according to which the desired user's speech signal can be detected:

$$x(t)=m(t)-h(t)*y'(t)-k(t)*z'(t) \quad (6)$$

A filter is required for compensating external signal z(t), which filter realizes impulse response k(t). The filter can be constructed using discrete components, but preferably it is realized digitally in processor 34. Even traditional adaptive echo canceling algorithms can be used for estimating signals y(t) and z(t).

The acoustic coupling between microphone capsule 13 and error microphone 14 can be determined also during the operation of the device. This can be carried out by comparing the microphone signals m(t) and z'(t). When signal y'(t) is 0 and such a moment is found when the user of the device is not speaking, also x(t) is 0. In this case the remaining m(t) is essentially convolution k(t)*z'(t). Transfer function K(ω) can be determined from the division ratio of frequency space simply:

$$M(\omega)/Z'(\omega)=K(\omega)Z'(\omega)/Z'(\omega)=K(\omega) \quad (7)$$

Finally, the transfer function can be converted into the impulse response k(t) of time space using inverse Fourier-transform. This operation can be used e.g. for determining the acoustic leak of earphone unit 11 or as a help to speech synthesis e.g. when editing a user's speech.

When detected in the auditory tube 10, human speech is somewhat distorted, because typically high frequencies are more attenuated in the auditory tube 10.

By comparing in environment with little or preferably no noise at all, the differences between speech signals from microphone capsule 13 detecting speech in the auditory tube 10 and speech signals received by external error microphone 14, it is possible to determine the transfer function directed at the speech signal by the auditory tube utilizing e.g. the above described method. Based upon determining the transfer function it is possible to realize in processor 34 a filter which can be used for compensating the distortion in the speech signal caused by the auditory tube. In this case a better voice quality is obtained.

In environment with little noise external error microphone 14 can be used even in stead of main microphone 13. It is possible to realize the choice between microphones 13 and 14 e.g. by comparing the amplitude levels of the microphone signals. In addition to this the microphone signals can be analyzed e.g. using a speech detector (VAD, Voice-Activity Detection) and further through correlation calculation, with which one can confirm that signal z'(t) arriving in error microphone 14 has sufficient resemblance with the processed signal x(t). These actions can be used for preventing noise of nearby machinery or other corresponding source of noise and speech of nearby persons from passing on after the processor. When error microphone 14 is used instead of microphone capsule 13 it is possible to obtain better voice quality in conditions with little noise.

FIG. 4 presents in more detail the internal construction of earphone unit 11. The signals from microphone capsule 13 and error microphone 14 are amplified in amplifiers 30 and 36 after which they are directed through A/D-converters 31 and 35 to processor 34. When speech signal or MLS-signal from generator 50 is transferred to the user's auditory tube 10 they are transferred through D/A-converter 33 and amplifier 32 to ear capsule 12. Program codes executed by processor 34 are stored in memory 37, which is used by processor 34 also for storing e.g. the interim data required for determining impulse response h(t). Controller 38, which typically is a microprocessor, the required A/D- and D/A-converters 39 and processor 34 with memory 37 convert both the incoming and outgoing speech into the form required by transfer path 40. Transfer of speech into both directions can be carried out in either analogue or digital form to either external terminal device 121 (FIG. 13) or device 100, 110 (FIGS. 11A, 11B and 12) built in connection with earphone unit 11. The required A/D- and D/A-conversions are executed with converter 39. Also the power supply to earphone unit 11 can be carried out over transfer path 40. If earphone unit 11 has been designed for wireless operation, the required means of transmitting and receiving 111, 113 (FIG. 12A) and the power supply (e.g. a battery, not shown in the figure) are placed e.g. in the ear-mounted part.

If both the user of earphone unit 11 and his speaking partner are talking simultaneously, a so-called "double-talk" situation occurs. In the traditional "double-talk" detection of mobile telephones speech detectors are used in both the channel which transfers speech from the user to the mobile communication network (up-link) and in the channel which receives speech from the mobile communication network (down-link). When the speech detectors of both channels indicate that the channels indicate speech, the teaching of the adaptive echo cancellator is temporarily interrupted and its settings are saved. This state can be continued as long as the situation is stable, after which the attenuating of the microphone channel is started. Interrupting the teaching of the echo cancellator is possible because the eventual error is at least in the beginning lower than the up-link and down-link signals. In case of earphone unit 11 the traditional detection of "double talk" cannot be applied without problems, because a smallest error in determining impulse response h(t) will produce.an error which is of the same order than original signal x(t). In principle the problems arising could be avoided by giving priority to information transferred to one of the directions, but this solution is not attractive from the user's point of view. In this case users would experience interruptions or high attenuation in speech transfer. A better solution is achieved by striving for as good as possible separation of signals transferred to different directions.

Figure 7:
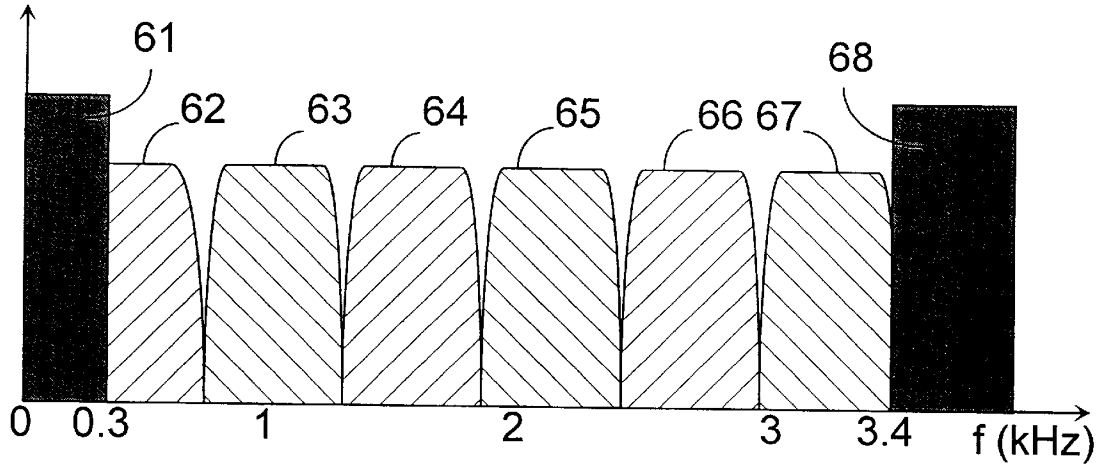
FIG. 7 presents the band limiting frequencies used in an embodiment according to he invention.
Figure 14:
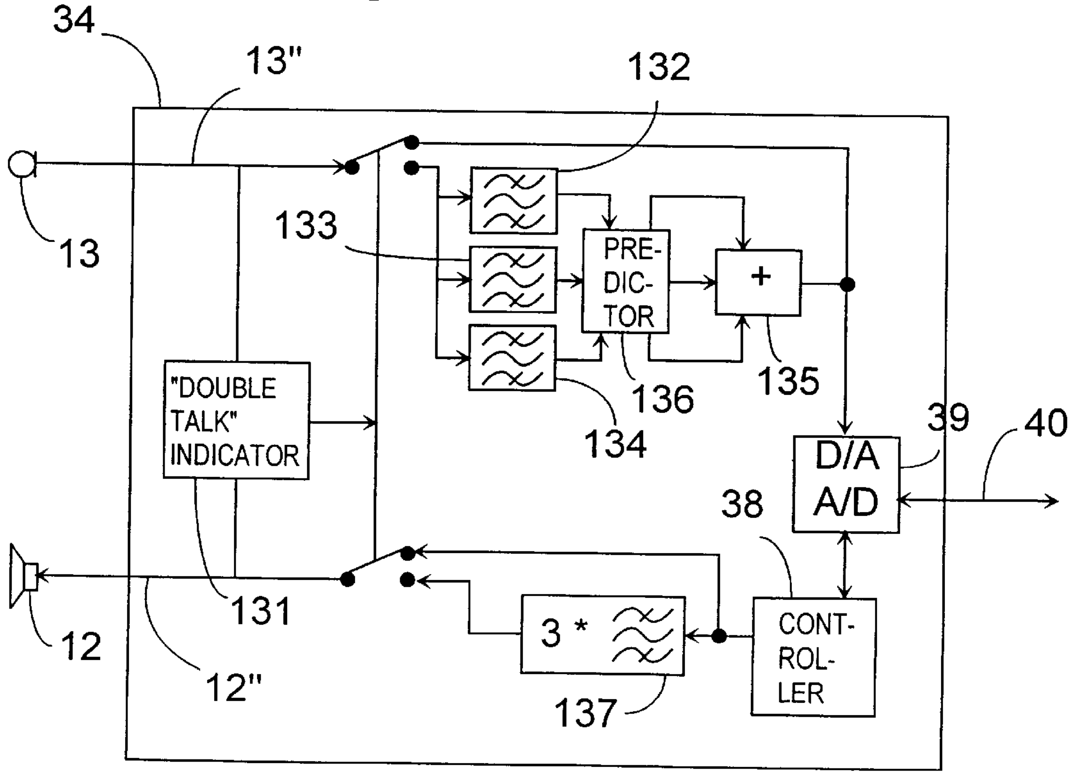
FIG. 14 presents the blocks of digital signal processing carried out in the earphone unit according to the invention.

FIG. 14 presents an embodiment in which microphone signal 13" and ear capsule signal 12" transferred to different directions are separated from each other using band-pass filters 132, 133, 134 and 137. The band-pass filters divide the speech band into sub-bands (references 61–68, FIGS. 7–10), in which case ear capsule 12 can be run on part of the sub-bands and the signal from microphone capsule 13 is correspondingly forwarded only on sub-bands which remain free. FIG. 7 presents an example of sub-bands, in which speech signal is transferred to both directions on three different frequency bands. In telephone systems the speech band is typically 300 to 3400 Hz. Out of the signal from microphone capsule 13 in this case frequency bands 300 to 700 Hz, 1.3 to 1.9 kHz and 2.4 to 3.0 kHz, or sub-bands 62, 64 and 66, are utilized directly. The signal repeated by ear capsule 12 contains correspondingly frequency bands 700

Hz to 1.3 kHz, 1.9 to 2.4 kHz and 3.0 to 3.4 kHz, or sub-bands 63, 65 and 67. In traditional mobile telephone communication frequency bands below 300 Hz (reference 61) and higher than 3.4 kHz (reference 68) are not used. The number of sub-bands has not been limited for reasons of principle, but to the more sub-bands the frequency range in use is divided, the better voice quality is obtained. As a counterweight to this the required processing capacity increases.

The above described utilizing of sub-bands needs preferably not to be done in other than "double-talk" situations, which are detected using detector 131 (FIG. 14). When a "double-talk" situation is detected, band limiting is started using band-pass filters 132, 133, 134 and 137, the last of which comprises three separate filters for the signal from ear capsule 12. When speech communication is unidirectional again, the band limiting is stopped, in which situation signal 13" from microphone capsule 13 is connected directly to controller 38 and ear capsule signal 12" directly from controller 38 to ear capsule 12.

Digital signal processing enables improving speech quality during band limiting. The contents of the missing sub-bands can be predicted based upon adjacent sub-bands. This is realized e.g. in frequency level by generating the energy spectrum of a missing sub-band based upon the energy spectrum of the limiting frequency of the previous and the next known sub-band. Generating of the missing sub-bands can be carried out e.g. using curve adaptation of first or higher degree prior known to persons skilled in the art. Even with simple prediction methods, such as curve adaptation of first degree, in most situations a better voice quality is obtained compared to only band limited signal, although due to the far advanced human auditory sense speech signal is intelligible even without predicting the missing sub-bands. The predicting has been described in more detail in connection with the explanation of FIGS. 8 to 10. The predicting is realized using predictor 136 (FIG. 14) in the transmitting end. Band-pass filters 132, 133 and 134 and summing unit 135 are used in connection with the predicting.

Figure 8:
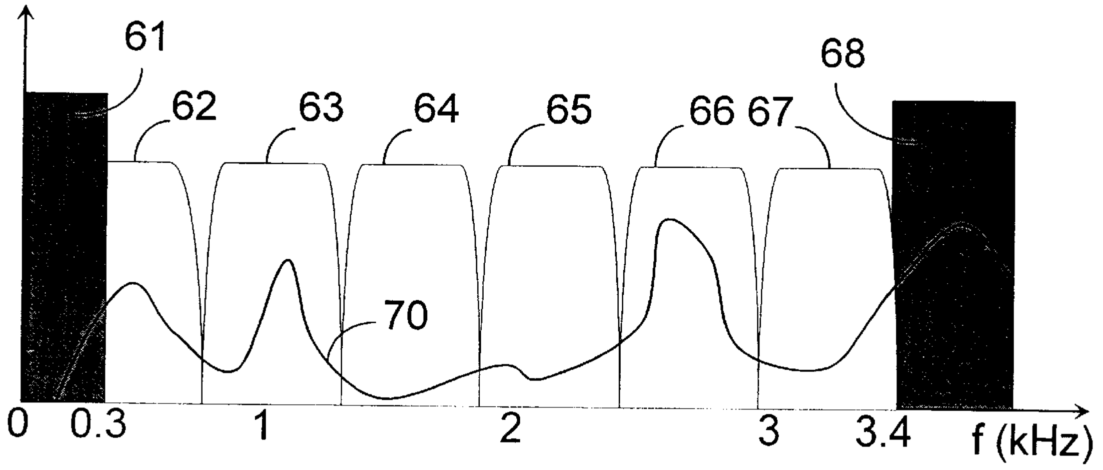
FIG. 8 presents microphone signal detected in the auditory tube at frequency level.
Figure 9:
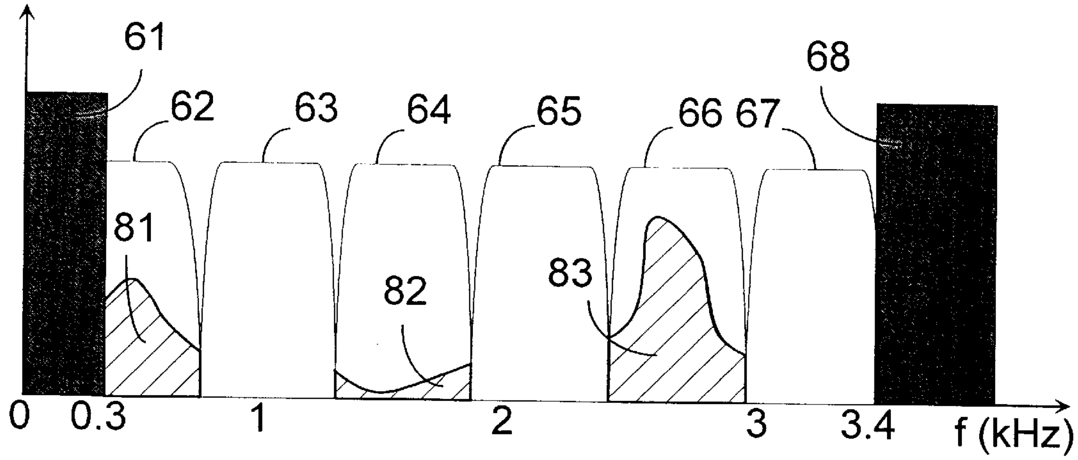
FIG. 9 presents band-limited microphone signal detected in the auditory tube at frequency level.

FIG. 8 presents signal 70 in frequency level as measured by microphone capsule 13 in auditory tube 10. The measuring band is wider than speech band 300 to 3400 Hz and accordingly signal 70 contains also frequency components under 300 Hz and over 3.4 kHz. In FIGS. 7 to 10 it is assumed that double-talk indicator 131 has detected a situation in which both the user of earphone unit 11 and his talking partner are speaking, due to which band limiting is on. FIG. 9 presents microphone signal 70 in frequency space, limited to sub-bands 62, 64 and 66, which signal in its new form consists of three separate components 81, 82 and 83 of the frequency space. If no kind of predicting of the missing sub-bands 63, 65 and 67 is carried out, band limited microphone signal 70 in frequency space looks like in FIG. 9 also in the receiving end, containing components 81, 82 and 83. In this case the speech signal is badly distorted because e.g. frequency peak 70' (FIG. 10) contained in band 63 is missing totally. In spite of this components 81, 82 and 83 form an understandable whole, because a human being is capable of understanding even a very distorted and imperfect speech signal.

Figure 10:
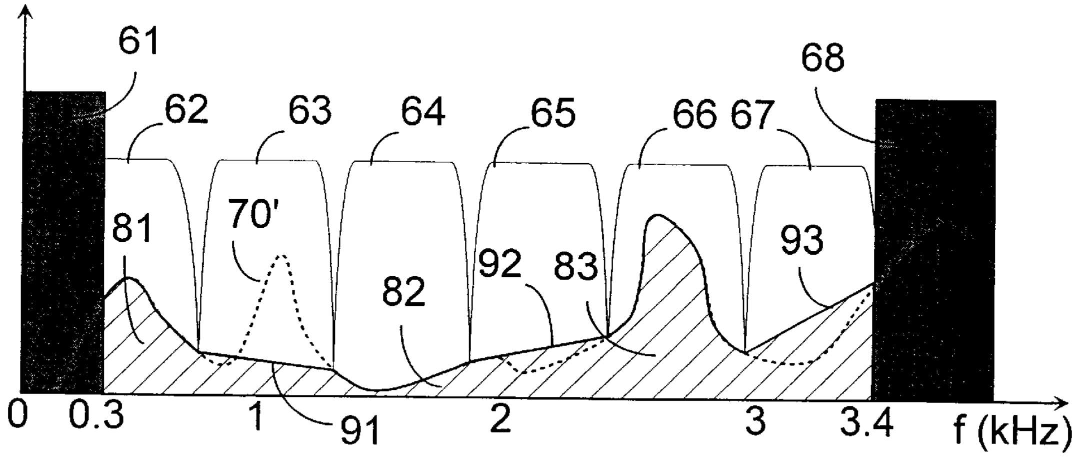
FIG. 10 presents band-limited microphone signal detected in the auditory tube at frequency level, in which the missing frequency bands have been predicted.

In FIG. 10, a curve adaptation of first degree has been adapted between signal components 81, 82 and 83 of FIG. 9, in which in all simplicity a straight line has been placed over the missing sub-bands. For example, straight line 91 is adjusted between the higher limit frequency (700 Hz) of sub-band 81 and the lower limit frequency (1.3 kHz) of sub-band 82, which gives the contents of sub-band 63. With corresponding predicting prediction 92 is obtained for sub-band 65 and prediction 93 for area 67. Let it be noticed that in order to obtain prediction 93 for area 67, it is also possible for predicting to use a frequency range higher than 3.4 kHz, even if it would be filtered away at a later stage. Correspondingly, sub-band 61 or lower than 300 Hz can be used, although it contains sounds of the human body, such as heartbeats and sounds of breathing and swallowing. The predicted, previously missing signal components 91, 92 and 93 are generated utilizing processor 34 and controller 38 before transferring to A/D- and D/A-converter 39 and transfer path 40.

In the above simple predicting of frequency bands in the frequency level more complicated methods of predicting can be used, in which e.g. the first and/or second derivate of microphone signal 70 are taken in account, or statistical analysis of microphone signal 70 can be carried out, in which case remarkably better estimates of the missing sub-bands can be obtained. With this method it is possible to obtain e.g. for frequency peak 70' in block 63 a prediction which is remarkably better than the now obtained prediction 91. Predicting of the missing bands requires however processing capacity the availability of which in most cases is limited. In this case one has to seek for a compromise between speech quality and the signal processing to be carried out.

Figure 11A:
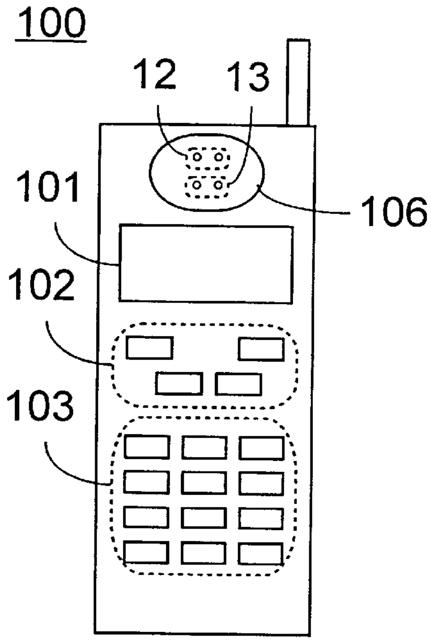
FIGS. 11A and 11B present a mobile station according to the invention.
Figure 11B:
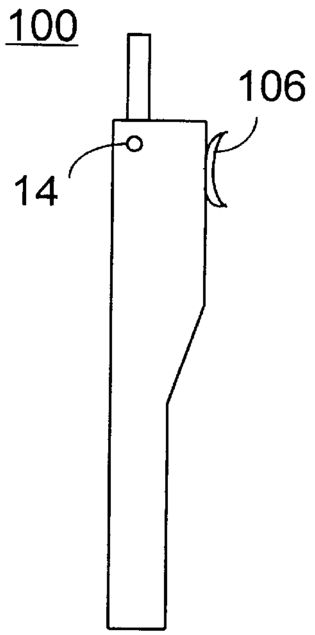

FIGS. 11A and 11B present another embodiment of earphone unit 11 according to the invention. In this embodiment earphone unit 11 has been integrated in connection with mobile station 100. Differently from a traditional mobile station, both ear capsule 12 and microphone capsule 13 have been placed in the same end of mobile station 100. Protective element 106 made of soft and elastic material, e.g. rubber, has been arranged in connection with ear capsule 12 and microphone capsule 13. The important function of the element is to prevent external noise 17' form entering the auditory tube 10 when mobile station 100 is lifted on ear 18 in operating position. Error microphone 14 used for eliminating external noise 17' has been placed in the side edge of mobile station 100. Because ear capsule 12 and microphone capsule 13 are placed next to each other, the distance between the human ear and mouth does not limit the dimensioning of mobile station 100, in which case mobile station 100 can be realized in even very small size. Limitations for the mechanical realization of mobile station 100 are set mainly by display 101, menu keys 102 and numeric keys 103, unless they are replaced with e.g. a speech-controlled user interface.

Figure 12:
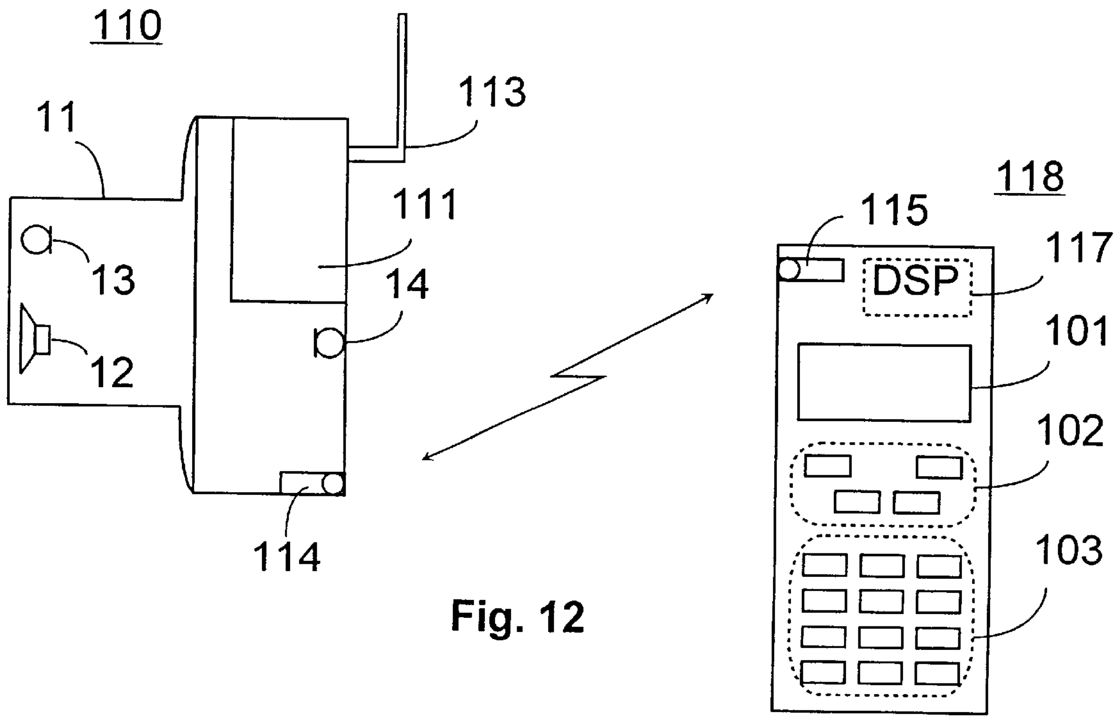
FIGS. 12 and 13 present mobile station arrangements according to the invention.

FIG. 12 presents another application example of earphone unit 11 according to the invention. In this application example simplified mobile station 111 with antenna 113 has been arranged in connection with earphone unit 11. Simplified mobile station 111 comprises a typical mobile station, e.g. a GSM mobile telephone, the typical radio parts prior known to persons skilled in the art and other parts of signal processing, such as the parts for handling the baseband signal for establishing a wireless radio connection to a base station (not shown in the figure). Differently from a traditional mobile station, part of user interface 101, 102, 103 has been placed in separate controller 118. Controller 118 can resemble a traditional mobile station or e.g. an infrared controller prior known from television apparatuses. It comprises display 101, menu keys 102, and numeric keys 103. It further comprises transceiver 115. Transceiver 115 has been arranged to transfer, e.g. in the infrared range, information between controller 118 and transceiver 114 arranged in connection with earphone unit 11 in order to control the operation of mobile station 111. Wireless mobile station 110, consisting of earphone unit 11 according to the invention, simplified mobile station 111 and transceiver 114, can using controller 118 operate preferably as a wireless mobile station mounted in one ear. The signal processing required for reducing the size of earphone unit 11, such as predicting missing frequency bands, can also be realized in processing means 117 arranged in controller 118.

Figure 13:
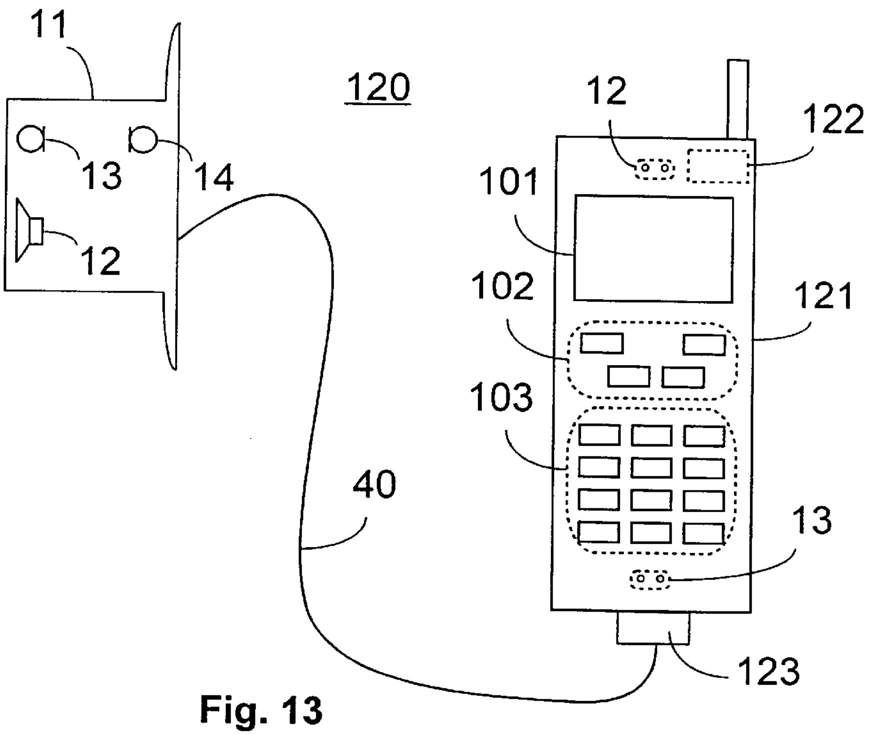

FIG. 13 presents mobile station system 120, which consists of earphone unit 11 according to the invention and traditional mobile station 121. Earphone unit 11 is connected to mobile station 121 using e.g. connection cable 40. Connection cable 40 is used for transferring speech signals in electric form from earphone unit 11 to mobile station 121 and vice versa in either analogue or digital form. In the solution in FIG. 13 it is possible to use earphone unit 11 for enabling the so called "hands-free" function. In traditional "hands-free" solutions a separate microphone has been needed, placed e.g. in connection with connection cable 40, but by using earphone unit 11 according to the invention a separate microphone is preferably not needed. Due to this "hands-free" function can be provided wirelessly using transceivers 114, 115 shown in FIG. 12, instead of connection cable 40, in earphone unit 11 and mobile station 121. Processing means 34, 37, 38 essential for the operation of earphone unit 11 can be placed either in earphone unit 11 itself, or preferably the functions are carried out in processing means 122 of mobile station 121, in which case it is possible to realize earphone unit 11 in very small size and at low manufacturing cost. If desired, processing means 34, 37, 38, 39 can also be placed in connector 123 of connection cable 40. In this case it is possible to connect earphone unit 11 with special connection cable 40 to a standard mobile station, in which specific processing means 122 are not needed.

The above is a description of the realization of the invention and its embodiments utilizing examples. It is self evident to persons skilled in the art that the invention is not limited to the details of the above presented examples and that the invention can be realized also in other embodiments without deviating from the characteristics of the invention. The presented embodiments should be regarded as illustrating but not limiting. Thus the possibilities to realize and use the invention are limited only by the enclosed claims. Thus different embodiments of the invention specified by the claims, also equivalent embodiments, are included in the scope of the invention.

What is claimed is:

1. An earphone unit to be connected to an ear, comprising sound reproduction means for converting an electric signal into an acoustic signal and for transferring it further into the auditory tube of the user of the earphone unit, and speech detection means for detecting the speech of the user of the earphone unit from the user's said same auditory tube, wherein it comprises means for determining an impulse response between said sound reproduction means and said speech detection means, means for separating sound signals produced into the auditory tube by said sound reproduction means from sound signals detected by said speech detection means based on said impulse response, and means for eliminating sound signals produced into the auditory tube by said sound reproduction means from sound signals detected by said speech detection means.

2. An earphone unit according to claim 1, wherein it further comprises means for eliminating external noise from sounds detected by said speech detection means.

3. An earphone unit according to claim 1, wherein it further comprises means for dividing the frequency band utilized by sound signals produced by said sound reproduction means and sound signals detected by said speech detection means into at least two parts.

4. An earphone unit according to claim 3, wherein it further comprises predicting means for predicting missing frequency bands created in connection with said division of frequency bands.

5. An earphone unit according to claim 1, wherein the sound reproduction means for converting an electric signal into an acoustic signal comprises one microphone transducer.

6. An earphone unit according to claim 1, wherein the speech detection means for detecting the speech of the user of the earphone comprises one microphone transducer.

7. A terminal device arrangement which comprises a terminal device which terminal device comprises means for two-way transfer of messages, and a separate earphone unit connected to an ear, which earphone unit comprises sound reproduction means for converting an electric signal into an acoustic sound signal and forwarding it into the auditory tube of the user of the earphone unit, and speech detection means for detecting the speech of the user of the earphone unit from said same auditory tube of the user, wherein it comprises means for determining an impulse response between said sound reproduction means and said speech detection means, means for separating sound signals produced into the auditory tube by said sound reproduction means from sound signals detected by said speech detection means based on said impulse response, and means for eliminating sound signals produced into the auditory tube by said sound reproduction means from sound signals detected by said speech detection means.

8. A terminal device which comprises means for two-way transfer of messages, sound reproduction means for converting an electric signal into an acoustic sound signal and forwarding it into the auditory tube of the user of the terminal device, and speech detection means for detecting speech, wherein said sound reproduction means and said speech detection means have been arranged in the terminal device close to each other in a manner for connecting both simultaneously to one and the same ear of a user, and the terminal device further comprising means for determining an impulse response between said sound reproduction means and said speech detection means, means for separating sound signals produced into the auditory tube by said sound reproduction means from sound signals detected by said speech detection means based on said impulse response, and means for eliminating sound signals produced into the auditory tube by said sound reproduction means from sound signals detected by said speech detection means.

9. A terminal device according to claim 8, wherein part of the user interface of the terminal device has been placed in a separate controller and that said controller and terminal device have been arranged to transfer information between each other utilizing at least one of the following communication methods: telecommunication connection by wire and wireless telecommunication connection.

10. A method of reproducing voice in a person's ear, said method comprising the steps of:

placing a transducer unit in or at the person's ear, transferring a speaker signal into the person's ear by the transducer unit;

a speech signal of the person being conducted inside the head from the person's vocal cords to the person's auditory tubes via the person's bone and soft tissue structure in response to speech of the person;

detecting a sound signal in or at the person's ear by the transducer unit, said sound signal comprising said speech signal and said speaker signal; and subtracting said transferred speaker signal from said sound signal.

11. A method according to claim 10 further including the steps of:

detecting a noise signal by a second microphone positioned to receive said signal from an external source; and subtracting said noise signal from said sound signal in order to improve detection of the speech signal.

12. A method according to claim 10 wherein when the speaker signal is transferred into the person's ear the speaker signal is transferred into the same ear as the ear in which the sound signal is detected.

13. An earphone unit to be connected to an ear, comprising:

sound reproduction means for converting an electric signal into an acoustic signal and for transferring it further into the auditory tube of the user of the earphone unit; and speech detection means for detecting the speech of the user of the earphone unit from the user's said same auditory tube, wherein it comprises:

means for determining an impulse response between said sound reproduction means and said speech detection means;

means for separating sound signals produced into the auditory tube by said sound reproduction means from sound signals detected by said speech detection means based on said impulse response;

means for eliminating sound signals produced into the auditory tube by said sound reproduction means from sound signals detected by said speech detection means;

means for dividing the frequency band utilised by sound signals produced by said sound reproduction means and sound signals detected by said speech detection means into at least two parts; and predicting means for predicting missing frequency bands created in connection with said division of frequency bands.

* * * * *